United States Patent [19]

VanDerPuy et al.

[11] Patent Number: 5,574,192
[45] Date of Patent: Nov. 12, 1996

[54] PROCESS FOR THE MANUFACTURE OF 1,1,1,3,3-PENTAFLUOROPROPANE

[75] Inventors: Michael VanDerPuy; Alagappan Thenappan, both of Cheektowaga, N.Y.

[73] Assignee: AlliedSignal Inc., Morris County, N.J.

[21] Appl. No.: 519,857

[22] Filed: Aug. 25, 1995

Related U.S. Application Data

[63] Continuation of Ser. No. 273,553, Jul. 11, 1994, abandoned.

[51] Int. Cl.$^6$ .................................................. C07C 17/08
[52] U.S. Cl. ............................................ 570/167; 570/168
[58] Field of Search ............................... 570/167, 168, 570/172

[56] References Cited

U.S. PATENT DOCUMENTS

| | | | |
|---|---|---|---|
| 2,560,838 | 7/1951 | Arnold | 260/653 |
| 2,942,036 | 6/1960 | Smith et al. | 260/653 |
| 4,078,007 | 3/1978 | Ferstandig | 260/653.7 |
| 4,967,024 | 10/1990 | Gumprecht et al. | 570/168 |
| 5,202,509 | 4/1993 | Laviron et al. | 570/167 |

FOREIGN PATENT DOCUMENTS

| | | | |
|---|---|---|---|
| 684687 | 4/1964 | Canada. | |
| WO90/08754 | 8/1990 | European Pat. Off. . | |
| 522 639 A1 | 1/1993 | European Pat. Off. . | |
| 0522639 | 1/1993 | European Pat. Off. | 570/167 |
| 1418930 | 10/1968 | Germany . | |
| 1146463 | 3/1969 | United Kingdom . | |

OTHER PUBLICATIONS

"Selective Additions of Polyhalogenated Compounds to Chloro Substituted Ethenes Catalyzed by a Copper Complex,"— M. Kotora and M. Hajek 44(2) React. Kinet. Catal. Lett. 415(1991).
Henne, "The Use of Inorganic Fluorides", *Organic Reactions*, vol. 2, 53–63 (1944).
Boutevin, et al. "Monofunctional Vinyl Chloride Telomers . . . ", 18 Eur. Polym. J. 675 (1982) in 97 Chem. Abstr. 182966c (1982).
Knunyants, et al., Catalytic Hydrogenation of Perfluoro Olefins, 55 Chem. Abst. 349f (1961).
"Partial Fluorination of Tetrahydrofuran with Cobalt Trifluoride"— J. Burdon et al., J. Chem. Soc.(C), 1739–1746(1969).
A. L. Henne et al., Fluoroethanes and Fluoroethylenes 58 J.Am.Chem.Soc.889–90(1936).

"Free Radical Additions Involving Fluorine Compounds . . . "— Paul Tarrant et al., Addition of Dibromodifluoromethane to Fluoroölefins, 77 J.Am.Chem.Soc., 2783–87 (1955).
"Heat–transfer agents", 125031q, Chem. Abs., p. 144, vol., 114, 1991.
"Aliphatic Difluorides"— A. L. Henne, et al., J.Am.Chem.Soc., pp. 938–940, vol. 61 (Apr. 1939).
"A New Fluorination Method"— A. L. Henne, J.Am.Chem.Soc., pp. 1569–1571, Jul., 1938.
"Fluorinated Derivatives of Propane, II"— A. L. Henne et al., Fluorinated Derivatives of Propane, pp. 2491–2495, Oct., 1938.
"Fluorination of Organic Compounds with Anhydrous Hydrogen Fluoride. Part II. An Investigation of Antimony Pentachloride Catalysed Fluorinations"— W. B. Whalley, J.S.C.I., pp. 430–433, vol. 66, Dec., 1947.
Asscher, et al., "Chlorine Activation by Redox–transfer . . . ", J. Chem. Soc. (1961) pp. 2261–2264.
Belbachir, et al., "Telomerization of Vinylidene Chloride I . . . " 185 Makromol. Chem. 1583–1595 (1984).
EP 381986 A Abstract, 1989.
EP 414370 Abstract as cited in 114 Chem.Abstr. 206550K (1991).
Henne, et al, "Fluorinated Derivatives of Propane. II", pp. 2491–2495, Oct. 1938.
English Abstract to EP 522638 (1993).
English Abstract to DE 3,903,336 (1990) as cited in 114 Chem. Abstr. 832 36b, p. 51.
Chen et al., "Telomerizations of Vinylidene Fluoride . . . " 38(2) Huaxue Xuebao 175–84, (Apr., 1980).
Chen et al., 94 Chem.Abstr. 1741840 (1981).

*Primary Examiner*—Alan Siegel
*Attorney, Agent, or Firm*—Jay P. Friedenson; Michele G. Mangini

[57] ABSTRACT

This invention is related to the preparation of hydrofluorocarbons (HFCs). Specifically, it relates to the fluorination of a compound of the formula:

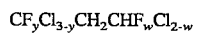

$$CF_yCl_{3-y}CH_2CHF_wCl_{2-w}$$

wherein w=0 or 1, and y=0–3, with hydrogen fluoride in the presence of a fluorination catalyst under conditions sufficient to produce a compound of the formula $CF_3CH_2CF_2H$.

$CF_3CH_2CF_2H$ or HFC 245fa may be used as a blowing agent, a propellant, and a heat transfer agent.

31 Claims, No Drawings

PROCESS FOR THE MANUFACTURE OF 1,1,1,3,3-PENTAFLUOROPROPANE

This application is a continuation of application Ser. No. 08/273,553 Filed Jul. 11, 1994, now abandoned.

BACKGROUND OF THE INVENTION

This invention relates to a novel method of manufacturing 1,1,1,3,3-pentafluoropropane, $CF_3CH_2CF_2H$, which is referred to in the art as HFC-245fa. Specifically, the invention relates to the fluorination with hydrogen fluoride of a compound of the formula:

$$CF_yCl_{3-y}CH_2CHF_wCl_{2-w}$$

wherein w=0, or 1, and y=0–3, in the presence of a fluorination catalyst to produce HFC-245fa.

HFC-245fa has physical properties, including a boiling point of about 14° C., which make it particularly attractive as a blowing agent. (See Ger. Often, DE 3,903,336, 1990 (EP 381,986 A)). It also has the ability to function as an aerosol propellant (U.S. Pat. No. 2,942,036 to Smith and Woolf) in a manner similar to trichlorofluoromethane, which is referred to in the an as CFC-11, and as a heat transfer agent. (Jpn. Kokai Tokyo Koho JP 02,272,086 in 114 Chemical Abstracts 25031q (1991)).

Traditionally, chlorofluorocarbons (CFCs) like CFC-11 and dichlorodifluoromethane (CFC-12) have been used as refrigerants, blowing agents and propellants. These materials, however, are believed to contribute to stratospheric ozone depletion. The fluorocarbon industry therefore has focused its attention on developing stratospherically safer alternatives to these materials. HFC-245fa is a candidate replacement material since it functions in substantially the same way as the CFCs but is zero ozone depleting. Because the demand for these and other low or zero ozone depleting materials will increase dramatically in the future, commercially viable processes for their preparation are needed.

Only two methods for manufacturing HFC-245fa (which are not hydrofluorination reactions) are reported in the art. However, these methods are not without their shortcomings. Knunyants, et at., *Catalytic Hydrogenation of Perfluoro Olefins*, 55 Chemical Abstracts 349f (1961), discloses the reduction of 1,1,1,3,3-pentafluoropropene to HFC-245fa. Because this process includes multiple steps, it is inefficient and uneconomical. Burdon, et at., *Partial Fluorination of Tetrahydrofuran with Cobalt Trifluoride*, J. Chem. Soc. (C), 1739 (1969), discloses the elemental fluorination of tetrahydrofuran to produce HFC-245fa. This process suffers the disadvantage that it produces a host of other by-products, thus reducing the yield of the desired product.

As far as hydrofluorination reactions are concerned, there are no such methods for the production of HFC-245fa reported in the art, let alone fluorination reactions which use 1,1,1,3,3-pentachloropropane ($CCl_3CH_2CHCl_2$) as the starting material to produce HFC-245fa. Although the conversion of —$CCl_3$ groups to —$CF_3$ groups is well-known in the art, attempts to fluorinate terminal —$CHCl_2$ or —CHClF groups to—$CHF_2$ groups in compounds having more than two carbons, (in particular compounds of the formula $RCH_2CHCl_2$ and $RCH_2CHFX$ wherein X is Cl or Br and R is an alkyl group having at least one carbon atom), have not been successful. See Henne, et al., *Fluoroethanes and Fluoroethylenes*, 58 J. Am. Chem. Soc. 889 (1936).

Tarrant, et al., *Free Radical Additions Involving Fluorine Compounds. IV. The Addition of Dibromodifluoromethane to Some Fluoroolefins*, 77 J. Am. Chem. Soc. 2783 (1955) report the fluorination of compounds of the type $CF_2BrCH_2CHFBr$ with hydrogen fluoride (HF) in the presence of a Sb(V) salt catalyst, such as $SbCl_5$ and $TaF_5$. However, this method produced only a 14% yield of $CF_3CH_2CHFBr$ at 125° C., and only a modest improvement in yield at 170° C. Even at elevated temperatures, no HFC-245fa was produced.

DESCRIPTION OF THE INVENTION

We have discovered that the drawbacks associated with the prior art processes for manufacturing 1,1,1,3,3-pentafluoropropane or HFC-245fa can be eliminated by the process of our invention. That is, we have discovered an efficient and economical means of manufacturing HFC-245fa on a commercial scale, which uses readily available raw materials and which produces HFC-245fa in high yield.

The invention relates to a process for manufacturing 1,1,1,3,3-pentafluoropropane comprising:

1) reacting a compound of the formula:

$$CF_yCl_{3-y}CH_2CHF_wCl_{2-w}$$

wherein w=0 or 1, and y=0–3, with hydrogen fluoride in the presence of a fluorination catalyst under conditions sufficient to produce a compound of the formula $CF_3CH_2CF_2H$; and 2) optionally recovering a compound of the formula $CF_3CH_2CF_2H$.

The organic starting materials corresponding to the formula $CF_yCl_{3-y}CH_2CHF_wCl_{2-w}$, wherein w=0 or 1, and y=0–3, include $CCl_3CH_2CHCl_2$, $CF_3CH_2CHCl_2$, $CFCl_2CH_2CHCl_2$, $CF_2ClCH_2CHCl_2$, $CFCl_2CH_2CHClF$, $CF_2ClCH_2CHFCl$, and $CF_3CH_2CHFCl$. The preferred starting material is $CCl_3CH_2CHCl_2$.

These materials are not commercially available. However, they may be prepared by any means well-known in the art. See, for example, B. Boutevin, et al., *Monofunctional Vinyl Chloride Telomers. I. Synthesis and Characterization of Vinyl Chloride Telomer Standards*, 18 Eur. Polym. J. 675 (1982) in 97 Chemical Abstracts 182966c (1982); and Kotora, et al., *Selective Additions of Polyhalogenated Compounds to Chloro Substituted Ethenes Catalyzed by a Copper Complex*, 44(2) React. Kinet. Catal. Lett. 415 (1991). See also the method disclosed in Examples 1 and 2 below. When $CCl_3CH_2CHCl_2$ is the starting material, it is preferably prepared according to the method provided in Example 1 below. Alternatively, $CCl_3CH_2CHCl_2$ may be prepared by the reduction of $CCl_3CH_2CCl_3$ (see Example 2) as well as by photochlorination of $CCl_3CH_2CH_2Cl$.

Any water in the HF will react with and deactivate the fluorination catalyst. Therefore, substantially anhydrous HF is preferred. By "substantially anhydrous" we mean that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from AlliedSignal Inc. of Morristown, N.J.

Based on reaction stoichiometry, the required mole ratio of HF to organics (i.e., $CF_yCl_{3-y}CH_2F_wCl_{2-w}$) is 5-y-w (or the number of chlorine atoms in the organic starting material) to 1.0. HF is preferably used in an amount from about 1 to about 15 times the stoichiometric amount of HF to organics, and more preferably from about 6 to about 15 times the stoichiometric amount of HF to organics.

Fluorination catalysts useful in the process of the invention include: (I.) pentavalent antimony, niobium, arsenic and tantalum halides; (II.) pentavalent antimony, niobium, arsenic and tantalum mixed halides; and (III.) mixtures of pentavalent antimony, niobium, arsenic and tantalum halide catalysts. Examples of catalysts of group (I.) include antimony pentachloride and antimony pentafluoride. Examples of catalysts of group (II.) include $SbCl_2F_3$ and $SbBr2F_3$. Examples of catalysts of group (III.) include a mixture of antimony pentachloride and antimony pentafluoride.

Pentavalent antimony, niobium, arsenic and tantalum halides are commercially available, and mixed halides thereof are created in situ upon reaction with HF. Antimony pentachloride is preferred because of its low cost and availability. Pentavalent antimony mixed halides of the formula $SbCl_nF_{5-n}$ where n is 0 to 5 are more preferred. The fluorination catalysts used in this invention preferably have a purity of at least about 97%. Although the amount of fluorination catalyst used may vary widely, we recommend using from about 5 to about 50%, or preferably from about 10 to about 25% by weight catalyst relative to the organics.

It may be advantageous to periodically regenerate the catalyst due to the dissociation of the pentavalent catalyst over time. This may be accomplished by any means well known in the art. The catalyst may be regenerated, for example, by adding chlorine (in an amount of from about 1 to about 10 mole percent relative to the amount of pentavalent catalyst initially present in the reactor) to the combination stream comprised of organics of the formula $CF_yCl_{3-y}CH_2CHF_wCl_{2-w}$, and the recycled stream comprised of under-fluorinated materials and HF. The chlorine, which is continuously added to the process of this invention when operating in a continuous mode (and periodically added when operating in a batch mode), oxidizes the catalyst from the trivalent to the pentavalent state. One of ordinary skill in the art can readily determine without undue experimentation the amount of chlorine to be added in order to optimize the use of the catalyst.

The temperature at which the fluorination reaction is conducted and the period of reaction will depend on the starting material and catalyst used. One of ordinary skill in the art can readily optimize the conditions of the reaction without undue experimentation to get the claimed results, but the temperature will generally be in the range of from about 50° to about 175° C., and preferably from about 115° to about 155° C., for a period of, for example, from about 1 to about 25 hours, and preferably from about 2 to about 8 hours.

Pressure is not critical. Convenient operating pressures range from about 1500 to about 5000 KPa, and preferably from about 1500 to about 2500 KPa.

The equipment in which the fluorination reaction is conducted is preferably made of corrosion resistant material such as Inconel or Monel.

HFC-245fa may be recovered from the mixture of unreacted starting materials, by-products, and catalyst by any means known in the art, such as distillation and extraction. As illustrated in Example 3, at the end of the heating period, i.e. the amount of time for complete reaction in batch mode operations, the fluorination reaction product and remaining HF may be vented through a valve on the autoclave head, which in turn is connected to an acid scrubber and cold traps to collect the product. Alternatively, unreacted HF and organics may be vented and condensed, and the HF layer recycled to the reactor. The organic layer can then be treated, i.e. washed with an aqueous base, to remove dissolved HF and distilled. This isolation procedure is particularly useful for a continuous fluorination process. Under-fluorinated materials, such as $CF_3CH_2CHFCl$, may be recycled in subsequent runs.

In another embodiment, the invention relates to a process for the manufacture of 1,1,1,3,3-pentafluoropropane which comprises:

1. reacting $CCl_4$ and vinyl chloride in the presence of a telomerization catalyst under conditions sufficient to produce a compound of the formula $CCl_3CH_2CHCl_2$;
2. reacting a compound of the formula $CCl_3CH_2CHCl_2$ with hydrogen fluoride in the presence of a fluorination catalyst under conditions sufficient to produce a compound of the formula $CF_3CH_2CF_2H$; and
3. optionally recovering a compound of the formula $CF_3CH_2CF_2H$.

The telomerization of vinyl chloride by reaction with carbon tetrachloride to produce $CCl_3CH_2CHCl_2$ is known in the art. See, for example, B. Boutevin, et al., *Monofunctional Vinyl Chloride Telomers. I. Synthesis and Characterization of Vinyl Chloride Telomer Standards*, 18 Eur. Polym. J. 675 (1982) in 97 Chemical Abstracts 182966c (1982); and Kotora, et al., *Selective Additions of Polyhalogenated Compounds to Chloro Substituted Ethenes Catalyzed by a Copper Complex*, 44(2) React. Kinet. Catal. Lett. 415 (1991).

The starting materials for the telomerization reaction, i.e. carbon tetrachloride and vinyl chloride, are available from commercial sources. The molar ratio of $CCl_4$ to vinyl chloride is about 0.5:10, preferably about 1:8 (in order to minimize the formation of higher telomers), and most preferably about 1:5.

The telomerization of vinyl chloride can be initiated by any commercially available catalyst known in the art to be useful in initiating and catalyzing the telomerization of carbon tetrachloride and vinyl chloride. Suitable catalysts include, but are not limited to, organic peroxides, metallic salts, and metal carbonyls. Copper and iron salt catalysts, such as cuprous chloride (CuCl), cuprous iodide (CUI), and iron chloride ($FeCl_2$), are preferred. The amount of catalyst used in the telomerization reaction is at least about 0.1 to about 50 mmol, and preferably about 1 to about 20 mmol per mole of organics (i.e., $CCl_3CH_2CHCl_2$).

An amine co-catalyst, such as an alkanol amine, alkyl amine, and aromatic amine, may optionally be used in order to allow for the use of milder conditions in the telomerization process. Examples of suitable amine co-catalysts include ethanol amine, butyl amine, propyl amine, benzylamine, and pyridine. 2-propylamine is the most preferred co-catalyst. Such co-catalysts are commercially available. When a co-catalyst is used, it should be used in an amount from about 1 to about 10 moles per mole of catalyst, i.e., e.g. copper salt.

In order to dissolve the catalyst, a solvent, which is inert to the reactants and the desired product, may be used in the telomerization reaction. Suitable solvents include, but are not limited to, commercially available acetonitrile, dimethylsulfoxide, dimethylformamide, tetrahydrofuran, isopropanol, and tertiary butanol. Acetonitrile is preferred because of ease of handling and stability. The amount of solvent used ranges from about 5 times the amount of catalyst used on a mole basis to about 80 percent of the total volume of the total telomerization reaction mixture (i.e., solvent, catalyst, co-catalyst, carbon tetrachloride, vinyl chloride), and more preferably between about 10 to 50 times the mount of catalyst used on a mole basis.

The temperature at which the telomerization reaction is conducted and the period of reaction will depend on the catalyst selected, the presence of a co-catalyst, and the solubility of the catalyst system in the solvent. One of ordinary skill in the art can readily optimize the conditions of the reaction without undue experimentation to get the claimed results but the temperature will generally be in the range of from about 25° to about 225° C., preferably from about 50° to about 150° C. The period of reaction will generally range from about 3 to about 72 hours, preferably from about 10 to about 24 hours.

Pressure is not critical.

Preferably the telomerization reaction is conducted in a conventional apparatus, such as an autoclave made of corrosion resistant materials such as Teflon and glass.

Preferably, the telomerization product is recovered from by-products, solvent, catalyst and co-catalyst prior to the fluorination reaction to substantially eliminate the production of by-products in the fluorination step. The telomerization product may be recovered by any means well known in the art such as distillation and extraction. Optionally, the telomerization product may be further purified by additional distillation.

Due to the toxicity of vinyl chloride, other procedures for preparing $CCl_3CH_2CHCl_2$ may be employed. See Example 2 (reduction of $CCl_3CH_2CCl_3$). Alternatively, $CCl_3CH_2CCl_3$ may be prepared according to the well-known telomerization reaction of vinylidene chloride with carbon tetrachloride.

EXAMPLE 1

Preparation of $CCl_3CH_2CHCl_2$ from $CCl_4$ and $CH_2\!=\!CHCl$

A 600-mL monel autoclave equipped with mechanical stirrer was charged with 1 g CuCl, 156.6 g $CCl_4$ and 75 mL acetonitrile. The contents were cooled in an ice bath, and the autoclave was closed and evacuated briefly. 36.7 g of vinyl chloride was then added, and the contents stirred and heated to 135° C. for 16 hours. The volatile materials were removed by distillation at atmospheric pressure. Distillation at 23 mm Hg resulted in 90.0 g (71% yield based on vinyl chloride added) of a colorless liquid. The identity of this liquid was confirmed via proton nuclear magnetic resonance ("NMR") to be $CCl_3CH_2CHCl_2$ (boiling point 72°–74° C. $^1$H NMR ($CDCl_3$): δ6.15 (t, 1H), 3.7 (d, 2H)).

EXAMPLE 2

Preparation of $CCl_3CH_2CHCl_2$ by reduction of $CCl_3CH_2CCl_3$

A 600-mL monel autoclave equipped with mechanical stirrer was charged with 199.9 g $CCl_3CH_2CCl_3$, 199.5 g isopropanol, and 4 g CuI. The autoclave was closed and evacuated briefly. The contents were heated to 120°–125° C. for 16 hours. The volatile materials, including by-product isopropyl chloride, were removed by rotary evaporation, leaving 200 g of residue. Analysis on a Varian gas chromatograph having a packed column ("GC Analysis") indicated $CCl_3CH_2CHCl_2$ and $CCl_3CH_2CCl_3$ in a ratio of about 1:2, respectively. Distillation at 29 mmHg resulted in 107.9 g of starting material (boiling point from about 105° to 107° C.), and 36.9 g (46% yield) of $CCl_3CH_2CHCl_2$ (boiling point from about 85° to 90° C.).

EXAMPLE 3

Fluorination of $CCl_3CH_2CHCl_2$ with $HF/SbCl_5$

A 600-mL monel autoclave equipped with mechanical stirrer was charged with 8.7 g $SbCl_5$ and cooled to −27° C. The autoclave was then evacuated and charged with 49.8 g of anhydrous HF. The contents were cooled to −40° C., and 44 g $CCl_3CH_2CHCl_2$ was added. The reactor was then connected to a packed column/condenser assembly. The condenser was maintained at −20° C. The reaction mixture was heated to 135° C. over 2.25 hours and maintained at that temperature for an additional 2 hours. During this heating period, the pressure in the autoclave was maintained from about 1965 to 2655 KPa (300–400 psig) by periodically venting pressure (HCl by-product) in excess of 2655 KPa (400 psig). Venting was done from the top of the condenser to a cold aqueous KOH scrubber which was connected to −78° C. cold trap. The reactor was then completely vented to the cold trap. 18.5 g of a colorless liquid were collected. The identity of this liquid was determined by GC analysis to be 84% $CF_3CH_2CHF_2$ (corresponding to a yield of 57%) and 11% $CF_3CH_2CHClF$.

EXAMPLE 4

Fluorination of $CF_3CH_2CHCl_2$ with $HF/SbF_5$

The experiment described in Example 3 was repeated except that $CF_3CH_2CHCl_2$ was used as the starting material. To the apparatus described in Example 3 was charged 8.2 g $SbF_5$, 41 g HF, and 37 g $CF_3CH_2CHCl_2$. (The $CF_3CH_2CHCl_2$ was obtained via the room temperature photochlorination of commercially available $CF_3CH_2CH_2Cl$.) This mixture was heated with stirring to about 130°–135° C. for 4.5 hours at a maximum operating pressure of 3450 KPa. 18.1 g (corresponding to a yield of 57%) of a colorless liquid were recovered. GC analysis identified the material as 94% pure HFC-245fa.

EXAMPLE 5

Fluorination of $CF_3CH_2CHCl_2$ with $HF/SbCl_5$ at 150°–160° C. and Low Operating Pressure The experiment described in Example 3 was repeated except that $CF_3CH_2CHCl_2$ was used as the starting material. To the apparatus described in Example 3 was charged 9.5 g $SbCl_5$, 47.9 g HF, and 34.6 g $CF_3CH_2CHCl_2$. This mixture was heated with stirring to about 150°–160° C. for 3.5 hours and maintained at that temperature for an additional 2 hours. The maximum operating pressure, controlled by periodic venting of by-product HCl, was 1280 KPa. GC analysis of the crude reaction product indicated that it contained 71% HFC-245fa.

As illustrated by the above-described Examples, HFC-245fa is produced in high yield without the use of high temperatures or pressures and without using large quantities of expensive catalysts.

What is claimed is:

1. A process for the manufacture of 1,1,1,3,3-pentafluoropropane which comprises:

a) reacting a compound of the formula:

$$CF_yCl_{3-y}CH_2CHF_wCl_{2-w}$$

wherein w=0 or 1, and y=0–3, with hydrogen fluoride in the presence of a fluorination catalyst under conditions sufficient to produce a compound of the formula $CF_3CH_2CF_2H$.

2. The process of claim 1 wherein the fluorination catalyst is selected from the group consisting of pentavalent antimony halide, pentavalent niobium halide, pentavalent arsenic halide, pentavalent tantalum halide; pentavalent antimony mixed halide, pentavalent niobium mixed halide, pentavalent arsenic mixed halide, pentavalent tantalum mixed halide, and mixtures thereof.

3. The process of claim 2 wherein the fluorination catalyst is a pentavalent antimony halide.

4. The process of claim 2 wherein the fluorination catalyst has the formula $SbCl_nF_{5-n}$, where n is 0 to 5.

5. The process of claim 2 wherein said compound of the formula $CF_yCl_{3-y}CH_2CHF_wCl_{2-w}$ is selected from the group consisting of $CCl_3CH_2CHCl_2$, $CF_3CH_2CHCl_2$, $CFCl_2CH_2CHCl_2$, $CF_2ClCH_2CHCl_2$, $CFCl_2CH_2CHClF$, $CF_2ClCH_2CHFCl$, and $CF_3CH_2CHFCl$.

6. The process of claim 4 wherein said compound of the formula $CF_yCl_{3-y}CH_2CHF_wCl_{2-w}$ is selected from the group consisting of $CCl_3CH_2CHCl_2$, $CF_3CH_2CHCl_2$, $CFCl_2CH_2CHCl_2$, $CF_2ClCH_2CHCl_2$, $CFCl_2CH_2CHClF$, $CF_2ClCH_2CHFCl$, and $CF_3CH_2CHFCl$.

7. The process of claim 5 wherein said compound of the formula $CF_yCl_{3-y}CH_2CHF_wCl_{2-w}$ is $CCl_3CH_2CHCl_2$.

8. The process of claim 6 wherein said compound of the formula $CF_yCl_{3-y}CH_2CHF_wCl_{2-w}$ is $CCl_3CH_2CHCl_2$.

9. The process of claim 8 wherein said $CCl_3CH_2CHCl_2$ is prepared by: reacting $CCl_4$ and vinyl chloride in the presence of a telomerization catalyst under conditions sufficient to produce a compound of the formula $CCl_3CH_2CHCl_2$.

10. The process of claim 5 wherein said reaction is conducted at a temperature of from about 50° to about 175° C.

11. The process of claim 10 wherein said reaction is conducted at a temperature of from about 115° to about 155° C.

12. The process of claim 9 wherein said reaction is conducted at a temperature of from about 115° to about 155° C.

13. The process of claim 10 wherein said reaction is conducted for a period of from about 1 to about 25 hours.

14. The process of claim 13 wherein said reaction is conducted for a period of from about 2 to about 8 hours.

15. The process of claim 12 wherein said reaction is conducted for a period of from about 2 to about 8 hours.

16. The process of claim 13 wherein the amount of HF used is about 1 to about 15 times the stoichiometric amount of HF to said compound of the formula $CF_yCl_{3-y}CH_2CHF_wCl_{2-w}$.

17. The process of claim 16 wherein the amount of HF used is about 6 to about 15 times the stoichiometric amount of HF to said compound of the formula $CF_yCl_{3-y}CH_2CHF_wCl_{2-w}$.

18. The process of claim 15 wherein the amount of HF used is about 6 to about 15 times the stoichiometric amount of HF to said compound of the formula $CF_yCl_{3-y}CH_2CHF_wCl_{2-w}$.

19. The process of claim 16 wherein said fluorination catalyst is present in an mount of from about 5 to about 50% by weight relative to the amount of compound of the formula $CF_yCl_{3-y}CH_2CHF_wCl_{2-w}$ present.

20. The process of claim 19 wherein said fluorination catalyst is present in an amount of from about 10 to about 25% by weight relative to the amount of compound of the formula $CF_yCl_{3-y}CH_2CHF_wCl_{2-w}$ present.

21. The process of claim 18 wherein said fluorination catalyst is present in an amount of from about 10 to about 25% by weight relative to the amount of compound of the formula $CF_yCl_{3-y}CH_2CHF_wCl_{2-w}$ present.

22. The process of claim 1 further comprising the step of recycling underfluorinated materials.

23. The process of claim 19 further comprising the step of recycling underfluorinated materials.

24. The process of claim 21 further comprising the step of recycling underfluorinated materials.

25. The process of claim 1 wherein the $CF_3CH_2CF_2H$ is recovered.

26. The process of claim 22 wherein the $CF_3CH_2CF_2H$ is recovered.

27. The process of claim 24 wherein the $CF_3CH_2CF_2H$ is recovered.

28. The process of claim 27 wherein said $CF_3CH_2CF_2H$ is recovered by distillation.

29. A process for the manufacture of 1,1,1,3,3-pentafluoropropane which comprises:
  a) reacting $CCl_4$ and vinyl chloride under conditions sufficient to produce a compound of the formula $CCl_3CH_2CHCl_2$; and
  b) reacting a compound of the formula $CCl_3CH_2CHCl_2$ with hydrogen fluoride in the presence of a fluorination catalyst to produce a compound of the formula $CF_3CH_2CF_2H$.

30. The process of claim 29 wherein said $CCl_3CH_2CHCl_2$ is recovered prior to step b.

31. The process of claim 30 wherein $CF_3CH_2CF_2H$ is recovered.

* * * * *